United States Patent [19]

Brochon et al.

[11] Patent Number: 4,668,779

[45] Date of Patent: May 26, 1987

[54] GEL-FORMING SEMISYNTHETIC POLYGALACTAN METALLIC OXIDE COMPLEX

[75] Inventors: Marie-José Brochon, Vanves; Anne-France Corot, Olivet, both of France

[73] Assignee: Societe a Responsabilite Limitee Dite: "Korano", Olivet, France

[21] Appl. No.: 582,434

[22] Filed: Feb. 22, 1984

[30] Foreign Application Priority Data

Feb. 23, 1983 [FR] France ............................... 83 03368

[51] Int. Cl.$^4$ ...................... C12P 19/06; C07H 23/00
[52] U.S. Cl. ................................... 536/121; 536/1.1; 536/114; 536/123; 435/243; 435/262
[58] Field of Search ................. 536/114, 1.1, 123, 121

[56] References Cited

U.S. PATENT DOCUMENTS

| | | | |
|---|---|---|---|
| 3,335,127 | 8/1967 | Polson | 536/114 |
| 3,423,396 | 1/1969 | Zabin | 536/114 |
| 3,476,741 | 11/1969 | Jonas | 536/114 |
| 3,753,972 | 8/1973 | Yaphe et al. | 536/114 |
| 3,849,395 | 11/1974 | Moirano | 536/114 |
| 4,057,509 | 11/1977 | Costanza et al. | 536/114 |
| 4,112,220 | 9/1978 | Carroll et al. | 536/114 |
| 4,312,979 | 1/1982 | Takemoto et al. | 536/114 |
| 4,430,322 | 2/1984 | Stardt et al. | 536/114 |

OTHER PUBLICATIONS

Young et al., *Enzymatic Hydrolysis of Agar and Properties of Bacterial Agarases*, Proc. 7th. International Seaw. Symp., Sapparo, Japan, 1971, pp. 469–472, Tokyo Press 1972.

*Primary Examiner*—Johnnie R. Brown
*Attorney, Agent, or Firm*—Karl F. Ross; Herbert Dubno

[57] ABSTRACT

A flake-powder preparation of a polygalactan having randomly interlaced chains of alternating D and L forms and bonded to fine grain aluminum oxide, silicon oxide and titanium oxide disposed throughout the powder and chemically bonded to the chains to form chemical complexes therewith, is used as a substitute for agar-agar as a culture medium. The powder is soluble in water upon heating to a temperature of 80° C. and forms a reversible gel upon cooling.

6 Claims, 4 Drawing Figures

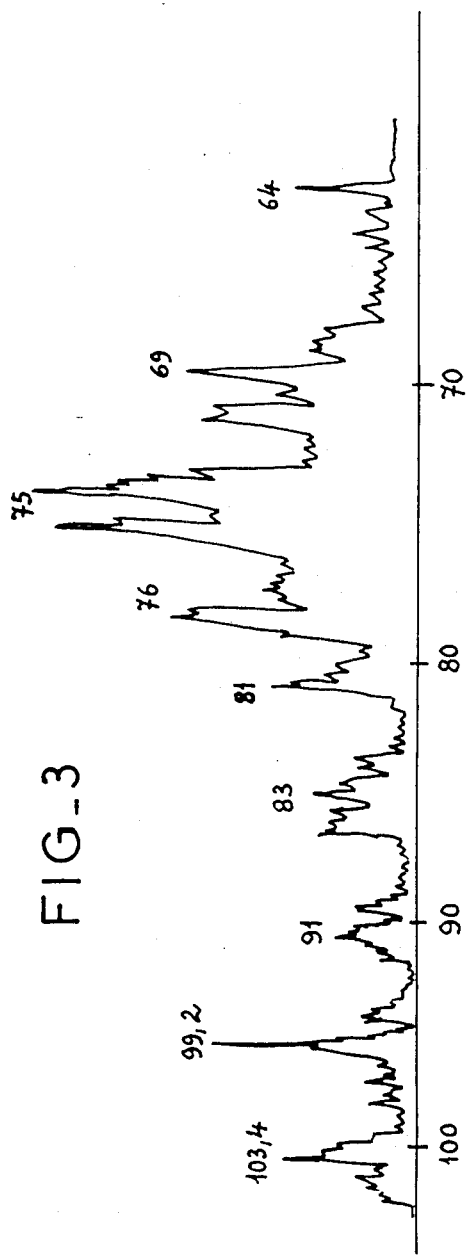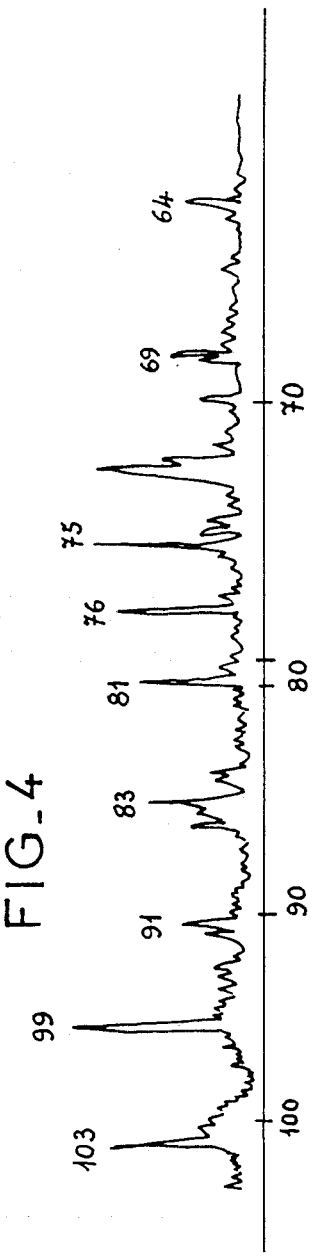

GEL-FORMING SEMISYNTHETIC POLYGALACTAN METALLIC OXIDE COMPLEX

FIELD OF THE INVENTION

Our present invention relates to a gel-forming semisynthetic substance capable of being used in media for the culture of plant organisms and microorganisms and especially as a complete or partial substitute for agar-agar in a culture medium for a variety of microorganisms. The invention also relates to the production of this new substance and to the method of culturing microorganisms thereon, i.e. to the use thereof.

BACKGROUND OF THE INVENTION

Techniques for isolating microorganisms currently in use in microbiology analysis laboratories, generally require the seeding or innoculating of the microorganism in or on a culture medium such that the development of the microorganism can take place under physical and chemical conditions which are rigorously predetermined and hence comparative from test to test. Generally the microorganism is seeded onto the surface of a solid culture medium constituted by nutritive elements contained in a gel, e.g. in the form of a layer in a petri dish which can be incubated. Each bacteria of the innoculum which survives, therefore, cends to grow in an isolated colony. Bacteria can be extracted from such colonies, such colonies can be counted or measured and determinations of colony growth and bacterial multiplication can be effected as a function of time. Therefore a number of known substances capable of forming, in an aqueous medium, gels which can solidify to form the matrix in or on which such colonies can develop. Such substances include synthetic macromolecular products, such as polyacrylamides and polycarboxyvinyl components, and mineral substances such as the silicates. However, these substances are not amenable to simple production of suitable gels because they are not reversible, i.e. they are not in the form of simple powders which can be converted into gels which can be melted and resolidified, or in the form of materials which can be converted into powders for ultimate conversion into gels as need arises. In the case of the synthetic macromolecular substances described it is generally necessary to add a polymerization agent to initiate the formation of the gel and this makes them incompatible with the need for simple powders which can be converted to gels only by the addition of water.

There are also a number of natural macromolecular substances capable of forming gels under the action of temperature or heat. Such is the case with gelatins and pectins which may be compatible with most components of a culture medium but which have only limited applications in bacteriology since with many microorganisms the gel is subject to attack by the microorganism, e.g. by bacteria.

As a practical matter at the present time, only the natural agar-agar has characteristics which permit practically universal use as a gel-forming agent for culture media in bacteriology. It has been to date the only product capable of giving reversible and stable gels at melting points (about 100° C.) substantially greater than the gelification temperature (about 40° C.). They are also characterized by a low tendency to attack by bacteria and low or no toxicity.

Naturally agar-agar or gelose is obtained by extraction of various marine algae of the Rhodophyceae family. It is a complex mixture of polysaccharides having a polygalactan skeleton formed by repetition of alternating units of (1→3)beta-D-galactose and (1→4)3,6-anhydro-alpha-L-galactose which can generically be referred to as agarose and in its commercial form is more or less substituted. Pure agarose does not occur in nature.

The result is a product which is approximately insoluble in water at 25° C. but which can be dispersed in water as the temperature approaches 100° C. to yield a colloidal solution whose viscosity varies as a function of the origin of the product and its concentration. At a concentration of at least 0.5% by weight, it forms, upon cooling, gels which have good stability and are reversible, i.e. they melt upon heating and rigidify upon cooling to a temperature below 40° C. These gels are characterized by their dynamic gelification temperature (passage from a solution state to the gel state on cooling) and by their isothermic gelification temperature (i.e. the minimum temperature at which a solution of agar-agar is able to be maintained indefinitely in liquid form without forming the gel). These parameters also vary as a function of the origin of the agar-agar, of the molecular weight thereof, of the production history and of the concentration of agar-agar in the gel.

The proportion of solid culture media using agar-agar as the gel forming substances generally involves mixing the agar-agar with suitable nutritive substances and then, after addition of water, solubilizing the mixture while assuring sterility by autoclaving.

There are commercially available dry powders which can be mixed with the nutritive substances or which contain the nutritive substances and are simply to be mixed with water.

The latter powders, generally nonsterile, are marketed in lots of at least 500 grams and the typical method of preparing a culture medium from them involves the following steps:

weighing out the desired quantity of powder (for example 40 grams per liter of water);

dissolving with boiling the weighed out quantity of powder in the requisite quantity of water;

placing the solution in an autoclave at 120° C. for at least 20 minutes; and distributing the solution to a multiplicity of culture vessels, e.g. petri dishes, manually or mechanically via a machine or automatic apparatus designed for this purpose.

These operations generally require about an hour and this, of course, precludes rapid preparation of unit doses of the powder, e.g. for a single culture test. In practice, it is necessary to prepare at least 20 to 40 petri dishes at a time which creates other disadvantages, such as the occupation of valuable laboratory space and time.

OBJECTS OF THE INVENTION

It is, therefore, the principal object of the present invention to provide a gel-forming composition which is capable of overcoming these disadvantages.

Another object of the invention is to provide an improved method of preparing a gel-forming composition which has greater versatility than even the agar-agar preparation utilized heretofore.

It is also an object of the invention to provide an improved method of culturing a microorganism whereby disadvantages of earlier culture methods are obviated.

Still another object of this invention is to provide an improved culture composition adapted to form a culture medium in a unit-dose form and simply with the addition of water.

SUMMARY OF THE INVENTION

These objects are attained, in accordance with the present invention with a new semisynthetic gel-forming substance capable of replacing agar-agar in all of its present applications and especially in its applications in culture media which is available in the form of a dry powder and whose use permits a significant reduction in the time for preparing a culture medium and even eliminates the prolonged periods hitherto considered necessary for dissolution and for autoclaving the product to ensure its sterility.

With the powder of the invention, sterile operations can be carried out, i.e. the powder can be transformed into a culture medium in the form of unit doses with dissolution, conditioning and manipulation in sterile vessels under sterile conditions, to provide a sterile gel-forming powder, and combining the sterile gel-forming powder with a requisite quantity of nutritive sterile powder, thereby forming a culture medium and eliminating the need for autoclaving before innoculation or seeding.

The gel-forming substance of the invention consists essentially of interlaced relatively short chains of unbranched polygalactans in which the unbranched D and L galactose moieties forms alternatively as in agar-agar and in which the interlaced chains are connected by inert metallic oxides, such as aluminum oxide, silicon oxide and titanium oxide which form part of the molecular structure of the gel-forming substance.

The latter is unlike any compound hitherto obtainable by extraction or synthesis and containing polygalactan skeletons and differs from agar-agar not only because the polygalactan chains are substantially shorter than those of agar-agar and are interlaced in a jumbled fashion, but also because these chains are connected to grains of metal oxides.

The weight ratio of metal oxides to polygalactans is inversely proportional to the length of the polygalactan chains and advantageously is between 10 and 80% (i.e. the product contains between 10 and 80% by weight metal oxides). The grain size of the metal oxides can range from 0.1 micron to 2000 microns.

The gel-forming substance according to the invention can, for convenience, be considered a polygalactan of synthesis-oxide and can be represented as PGS-O, a designation which we will use below to describe the new substance. The PGS-O has physical chemical properties close to those of agar-agar. For example, it is practically insoluble in water at 25° C. but is dispersed in water at temperatures starting from 80° C. and upwards thereof. PGS-O forms a gel upon cooling of the solution and, in solution in water, it forms a dispersion whose viscosity varies with its concentration. At a concentration of at least 0.5% by weight, it forms stable and reversible gels.

With respect to agarose, the PGS-O differs in the following respects:

at 80° C., PGS-O forms solutions in water while at the same temperature grains of agar-agar, of the same size, dispersed without dissolving. An essential characteristic of PGS-O therefore, is its complete solubility in water at 80° C. and the preferred dissolution temperature of 80° C. to 100° C.

The PGS-O chains are much shorter than the agarose chains. The length of the chains can be measured in terms of the molecular weight because they represent repetitions of the same unsubstituted disaccharide of a molecular weight of 325 ($H_2O$). The chains of PGS-O which are utilized in accordance with the invention have a molecular weight varying between 6,000 and 15,000 which corresponds to a number n of disaccharide moieties varying from about 19 to about 40 to 50. In agarose, the number n is more highly variable depending upon the source of the natural agar and usually is between 20 and 500. The molecular weight of the PGS-O units can be measured for each fabrication lot and can be indicated to the user as for example "product containing a PGS-O 6,000, a PGS-O 8,000 . . . " This is not possible with agar-agar. The determination can be subject to verification by molecular sieve, the agar-agar being always constituted by a mixture of polysaccharides having a common skeleton although more or less substituted.

The PGS-O powders are white and in the form of fine flakes having a thickness less than one hundredth of a mm. For PGS-O for use in bacteriology, the apparent density is much less than that of agar-agar. For example, the PGS-O of bacteriology quality with a molecular weight of 12,000 daltons and containing $Al_2O_3$, $TiO_2$ and $SiO_2$ in weight proportions of 66:17:16:01 (see Example 1) has an apparent density of 0.118 whereas bacteriological agar-agar for use in the same type of application has an apparent density of 0.384 in the form of grains. (Apparent density of a powder is a measure utilized in the formulation of pharmaceuticals and corresponds to the nonpacked weight of powder of a given volume. For example, a liter of the aforementioned PGS-O 66.17.16.01, nonpacked, weighs 118 grams. Hence apparent density utilizes a "poured" or unpacked weight of the powder.)

The true density of the PGS-O is substantially greater than that of agar-agar, i.e. is about 1 for agar-agar and about 1.3 for the PGS-O 66.17.16.01 by reason of the presence of the metal oxides in the latter. The PGS-O powders are compatible with granulation and compression. They tend to aglutinate and to bond to one another after compression. Consequently, it is possible to work not only with the powder grains, but also with granules or solid or compressed bodies which are not brittle and which decompose in water at 80° to 100° C. This is impossible with commercial agar-agar.

In the agarose gels the chains are parallel and ordered, whereas those of the PGS-O gels are interlaced randomly like the cellulose fibers of paper. This can be verified by X-ray diffraction studies from which it can be demonstrated that agarose has a repetitive crystalline-type structure while PGS-O shows only deflection halos without any regularity of structure indicative of an amorphous base.

Even chemical analysis shows the difference since agarose contains only polygalactans, whereas the PGS-O compositions of the invention always have a significant level of different metal oxides.

BRIEF DESCRIPTION OF THE DRAWING

The above and other objects, features and advantages of the present invention will become more readily apparent from the following description, reference being made to the accompanying drawing in which:

FIGS. 3 and 4 are nuclear magnetic resonants (NMR) spectrographs comparing agarose with a PGS-O according to the invention.

SPECIFIC DESCRIPTION

Figure 1:
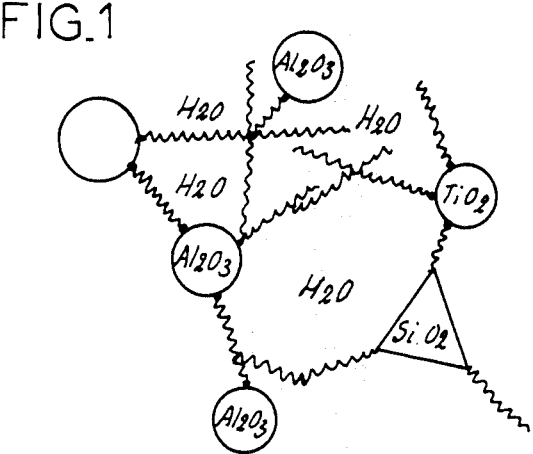
FIG. 1 is a diagram illustrating the composition of the PGS-O of the instant invention.

In FIG. 1 of the drawing, we have shown by wiggly lines, various length polygalactan chains which are interlaced and thus cross one another, while being bonded to grains of metal oxides as represented by the circles labeled $Al_2O_3$ and $TiO_2$ and by the triangle representing a tetrahedron labeled $SiO_2$. The unlabeled circle can be any of these metal oxides and can be bonded to other polygalactan chains of adjoining sections of the structure. The random or irregular pattern of interlacing should be apparent in FIG. 1 which also should be viewed as a three-dimensional structure with at least some of the polygalactan chains projecting out of the plane of the paper in either direction.

The difference between the NMR spectrographs of agarose and PGS-O can be readily ascertained by comparing FIG. 3 which represents the spectrum for agarose with FIG. 4 which represents the spectrum for PGS-O in which the PGS portion has a molecular weight of 12,000 daltons.

The NMR spectrum of FIG. 3 was obtained with commercial agar-agar by carbon 13 detection and shows 12 different principal signals corresponding to the carbon atoms and indicating that agarose possesses a regular structure with repetition of a single disaccharide unit. The signals recorded at 103.4 and 99.2 p.p.m. are attributed to the $C_1$ carbon of beta-D-galactopyranosyl and the $C_1$ carbon of alpha-L-galactopyranosyl. The signal at 62.4 p.p.m. is attributable to the $C_6$ carbon of the D-galactose. The other signals correspond either to the other 9 carbons constituting the disaccharide unit, the height of the peaks varying with the nature of the substituents on the carbon, or to the substituents such as the methoxyl group at 60 p.p.m..

With PGS-O (FIG. 4) the oxides provide absorption characteristics which cannot be found in agarose. In the zone corresponding to the polygalactans there are the 12 principal peaks corresponding to each of the carbons but the PGS-O does not have peaks corresponding to substituents on these carbons and hence the levels of the peaks are substantially fixed as contrasted with the commercial agar-agar. By contrast, moreover, it can be seen that as with agar-agar the peaks 103.4 and 99.2 characterize the alternating D and L forms of galactose.

Carbon 13 NMR spectrography consequently can be utilized for quality control during the production of PGS-O.

A final distinction which should be noted between agarose and PGS-O is that for equal weights of dry matter in the respective gel, the PGS-O gel is white and more or less opaque while agarose gel is more or less transparent.

It should be noted that the simple addition to natural agarose of proportions of metal oxides similar to those incorporated chemically into the PGS-O does not appear to modify the properties of the agarose and, especially, it does not give them properties common to PGS-O, e.g. the property of solubility as the temperature approaches 80° C.

According to another aspect of the invention, the polygalactan of the metal oxides (PGS-O) is synthesized by the use of enzyme producing microorganisms from oligosaccharides containing D and L galactoses, thereby synthesizing a nonbranched polygalactan skeleton in which the D and L forms alternate. The culture of these microorganisms is effected through a porous membrane covered with the fine powdered metallic oxide.

According to a feature of the invention, the microorganisms are first isolated from oligosaccharides formed by the hydrolysis of agarose. It is known that there are certain microorganisms which produce enzymes capable of hydrolyzing agarose and liberating the oligosaccharides; 4-0-beta-galactopyranosyl-(1→4) 3,6-anhydro-L-galactose, corresponding to a repetition of agarobiose units (oligosacchdrides A-B); and 0-3,6-anhydro-alpha-L-galactopyranosyl-(1→3)-beta-D-galactose, corresponding to repetitions of units of neoagarobiose (oligosacchrides B-A).

These enzymes break the B-D-(1-4) galactose and alpha-L-(1-3) galactose bonds in accordance with the following scheme:

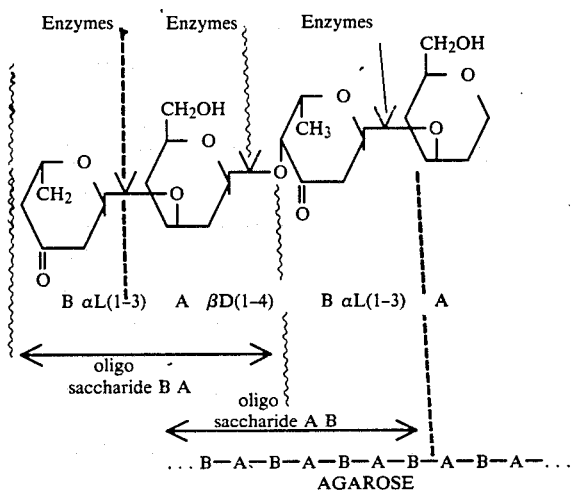

It can be noted that these enzymes have a reversible action and that the same microorganism which possesses the property of hydrolysis can be used inversely as a polymerizer. These oligosaccharides prepared from agarose, serve to enable selection of the polymerase producing microorganisms.

The isolation of microorganisms capable of synthesizing agarose or the synthesis polygalactan from the oligosaccharides is effected as follows:

Using the oligosaccharides formed from the hydrolysis of agarose and sterile techniques a synthetic solid culture medium is formed. To the surface of this medium is applied an innoculum of the myxoid bacteria known to produce capsulated polysaccharides. These bacteria are numerous and include Pseudomonas, Agrobacterium and Enterobacteria. Most advantageously the Pseudomonas Atlantis bacterium, well known for the hydrolysis of agarose can be used while the variety myxoid is selected to have mucous characterictics in the presence of polysaccharides.

Alternatively, by screening and by cloning it is possible to find a stem capable of synthesizing a polysaccharide whose structure is close to that of agarose, i.e. a stem is found which is capable, starting from oligosaccharides of the medium to produce long chains. These oligosaccharides, which contain 2, 3 or more units of disaccharides are utilized as initiators.

The micororganisms which are used are those which produce enzymes capable of elongating the chains by the addition of repeating hexose units, namely, the hexose transferases. The hexose transferases of the microorganisms can be extracted and permitted to function in vitro utilizing known enzymological techniques. The hexose transferase specific to the (1→3) and (1→4) bonds elongate the chains by the usual biological polymerization processes. The alternation of the D and L galactose takes place and the bonds 1→3 and 1→4 are obtained respectively by the action on the A - B oligosaccharides by a (1→3)-beta-D-galactose transferase and on the B-A oligosaccharide by a (1→4)-alpha-L-galactose transferase.

While screening is generally a time consuming process even when starting with marine bacteria, it is comparatively simple since one finds that the polysaccharide is insoluble in cold water or water at temperatures up to 50° C. Thus hundreds of colonies can be washed with retention only of those which form an insoluble mass.

It is thus possible to isolate the microbiological stems which are most productive and best for the genetic transfer.

The bacteria capable of synthesizing polygalactans close in structure to agarose starting from oligosaccharides of agarose are also able to effect such synthesis starting from oligosaccharides from other primary sources.

It is consequently advantageous to select as primary materials or sources those which already contain D and L galactose. The readily available natural products containing these hexoses are numerous, for example, the products of algae which are not used to produce agar, such as fucus which contains fucosane (sequences of 6-desoxy-D-galactose and 6-desoxy-L-galactose or D-fucose and L-fucose). From algae which produce agar-agar, the agar-agar can be recovered in the usual manner and the residue used as a source for producing the PGS-O according to the invention. This residue was customarily discarded in the past.

The transformation of the 6-desoxy-D-galactose and the 6-desoxy-L-galactose to D-galactose and 3,6-anhydro-L-galactose can be carried out by conventional chemical and biological techniques.

Apart from algae, the number of terrestrial organisms (vegetable and microorganisms) capable of producing D and L galactose sequences or derivatives of galactose such as pectins is considerable. Hence the choice of the material used as the starting material will depend usually upon the geographical region and on the nature of local industries at which the process is to be practiced.

From the starting materials, only the alternating L and D galactose sequences are retained. Consequently, apart from algae which produce agar-agar, it is possible to use algae which do not produce agar-agar (e.g. fucus) and to modify the sequences which are thus formed to obtain alternation of the L and D galactoses.

Figure 2:
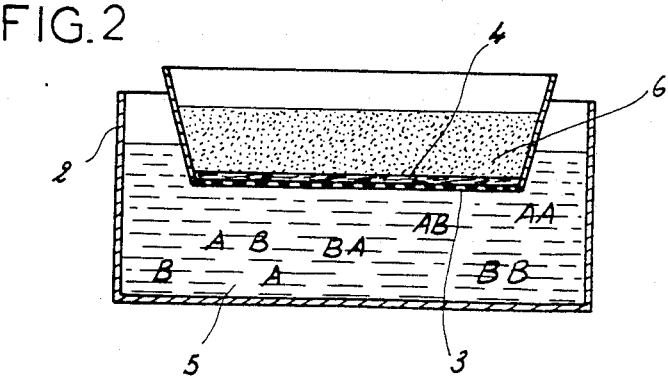
FIG. 2 is a vertical section through a device showing the formation of a PGS-O composition according to the invention.

The method of producing PGS-O according to the invention is illustrated diagrammatically in FIG. 2 of the drawing in which the vessel 2 holds the preparation and a porous member 3 is provided on which a layer or bed 4 of finely divided metal oxide is provided.

At 5 we have shown the nutritive medium containing the oligosaccharides or other precursors in accordance with the principles described and at 6 one can see the polygalactan synthesis oxide which is thus obtained.

A sterile solution of the oligosaccharides is formed, for example of an aqueous suspension containing 10% by weight of the residue of an algae production of agar-agar and from which the agar-agar has already been extracted. This solution also contains the bacterial growth factors which are necessary, such as a nitrogen source, vitamins and 0.2% caseine hydrolysate.

Utilizing this solution and in accordance with conventional techniques for membrane culturing of microorganisms, bacteria capable of producing the polygalactan is cultivated. The fine powder of metal oxides forming the bed 4 on the membrane 3 will generally contain finely divided aluminium oxide ($Al_2O_3$ neutral for chromotography) and titanium dioxide ($TiO_2$) on which are fixed the initiators. The bacteria culture is effected on the surface of the oxide grains and the oligosaccharide chains bond to them and grow in the formation of a continuous mesh as represented at 6 with the polygalactan chains chemically bonded to the oxides to form a complex therewith. Periodically this layer or mat 6 is removed and autoclaved to kill remaining bacteria and terminate the enzymatic activity. The membrane can be recoated with the powder and the process continued.

The autoclaved PGS-O, being insoluble in cold water, is washed and only the insoluble part is retained and dried to form a pasty product.

The paste is treated with methyl alcohol and is dried at high temperatures (about 140° C. under pH conditions strictly controlled to form hydrogen bonds on foils of polytetrafluoro-ethylene utilized to carry the product through the dryer).

A thin film of dry product with a thickness no greater than a hundredth of mm is formed on the polytetrafluoroethylene foil and upon scraping of the layer from this foil, flakes of the powder are obtained.

Depending upon the culture temperature the pH, the nitrogen source, the origin of the polysaccharides and the period of growth, the chains can be of greater or lesser length. The chains bond to the oxides in a network which promotes increased length of degree of bonding. When chains are excessively long, however, the oxides are eliminated and transparent gels are obtained and by maintaining a given set of parameters, polygalactans which are highly reproducible are obtained.

Oxide grains in the polygalactin-synthesis appear to confer a porosity to the gel and which had much greater than that of agar-agar although the network constituted by the gel is impermeable to bacteria. Only the chemical substances used in the culture medium diffuse rapidly in the gel constitutes an advantage for the preparation of the medium.

As the chains of PGS-O are shorter, the less difficulty there is in producing the product, the lower the melting point, the greater the fragility of the gel, the more dry material is required to obtain a solid gel, the greater the proportion of oxide which can be incorporated in the solid gel and the greater the porosity of the gel.

With increasing chain length, the difficulty of production increases and the less metal oxides are retained therein so that the gel approaches a transparent gel. In theory, therefore, it is possible to obtain gels of long chains of polygalactan which are transparent and have the same qualities as agarose but at a lower cost.

The quantity of PGS-O per liter, the proportions of oxides in the PGS-O and the lengths of the polygalactan chains are variables which permit a range of qualities to be obtained for many different applications and the following table is exemplary of various compositions which can be used. In this table, W is the weight in parts or percent of PGS and x, y and z represent the weights in parts or percent of the different oxides. For example, x represents the weight of $Al_2O_3$, small y the weight of $TiO_2$ and z the weight of $SiO_2$. The five columns illustrate five different PGS-O.

| Qualities of PGS-O | | | | | |
|---|---|---|---|---|---|
| W | 60 | 60 | 84 | 66 | 30 |
| x | 20 | 18 | 2 | 17 | 30 |
| y | 20 | 20 | 10 | 16 | 30 |
| z | 0 | 2 | 4 | 1 | 10 |

SPECIFIC EXAMPLES

The use of the gel-forming substance according to the invention in the production of a natural medium is described below in a number of Examples which are intended to be illustrative of the invention rather than limiting thereof:

EXAMPLE 1

Preparation of a Petri dish containing the MAC CONKEY nutritive medium

| Formula parts percent | |
|---|---|
| PGS-O 66.17.16.01 | 33.62% |
| consisting of: | |
| 66 grams of PGS, | |
| 17 grams of $Al_2O_3$ | |
| 16 grams of $TiO_2$ | |
| 1 gram of $SiO_2$ | |
| Peptone | 36.34% |
| Biliary salts | 2.72% |
| Sodium chloride | 9.08% |
| Lactose | 18.17% |
| Neutral Red | 0.052% |
| Crystal Violet | 0.018%. |

A sterile dose or unit quantity of this powder composition, i.e. 1.376 grams, is dumped into 25 ml of sterile distilled water under sterile conditions and heated to 80° C. for one minute. The solution is then poured into a sterile Petri dish of a diameter of 9 cm.

The layer is permitted to gel by cooling to room temperature and is ready for use without autoclaving.

The results were as follows:

The medium was a clear opaque salmon rose color.

Lactose+colonies were red, and lactose−colonies were yellow.

Only the enteric bacteria colonies developed.

A comparison made with the MAC CONKEY medium using natural agar-agar gave results which were the same except that the colonies are more visible than the opaque ground of the new medium.

EXAMPLE 2

Preparation of a double-layer medium

Two PGS-O gels of different qualities are superimposed to constitute the medium.

First case

A thick, porous absorbent layer of comparatively large thickness and on which microorganism development is somewhat difficult is cast to serve as a reservoir for water and nutritive elements utilizing PGS-O 30.30.30.10 and consisting essentially of:

| Layer A | |
|---|---|
| 30% | PGS |
| 30% | $Al_2O_3$ |
| 30% | $TiO_2$ |
| 10% | $CaHPO_4$ |

Above Layer A a fine layer (Layer B) with a thickness of 1 to 2 mm of a highly dense PGS-O which is translucent but with which it is difficult to obtain very high quality colonies, namely, PGS-O 96.02.02, i.e.

| Layer B | |
|---|---|
| 96% | PGS |
| 2% | $Al_2O_3$ |
| 2% | $TiO_2$ |

The upper translucent layer can also be replaced if desired by a high purity layer of agarose.

The combination is more economic than a medium consisting solely of agar-agar and which may be used for large scale cultures where kilograms of the culture medium may be necessary, e.g. in the production of seedlings.

The combination or double layer can be used for seedling cultures without difficulty.

Second case

The first layer providing a nutritive closed cell gel is cast at a temperature of 100° C. (Layer A).

After gel formation, a second layer of a gel at a melting point as low as possible, for example about 60° C. (Layer B) is cast on Layer A and contains red globules. Layers A and B have the compositions set forth below:

| | Layer A | Layer B |
|---|---|---|
| PGS | 66 | 40 short fibers |
| $Al_2O_3$ | 17 | 30 |
| $TiO_2$ | 16 | 30 |
| $SiO_2$ | 1 | — |

With this two-layer medium we can considerably save on the most expensive component, the red globules, and the formation of the medium is simplified because low temperatures can be used and the red globules are very sensitive to heat.

EXAMPLE 3

PGS-Os containing very short PGS chains and various proportions of metal oxides form gels in which substances diffuse chemically far more rapidly than in agar-agar. This gel is sufficiently solid to permit cultures on the surface of bacteria and other microorganisms. Indeed, they can be used for so-called continuous culture media, either by casting the gel on a support containing the nutritive medium, for example on blotting paper impregnated with a solution of the nutritive substances and dried. The solution of these substances and their diffusion in the gel is extremely rapid. Alternatively, the gel can be cast on a porous support such as blotting paper or a reusable porous support such as fritted or sintered stainless steel impregnated with the nutritive substances and which permits repetition of such impregnation to generate continuous cultures of microorganism colonies and particularly of seedlings. These processes are particularly advantageous for mutant research into bacteria and plants.

The advantages of the new gel-forming substances of the invention thus have been developed above and can be summarized as follows:

The PGS-O which is soluble like the nutritive powders without being autoclaved permits preparation in the same sterile receptacle and sterile handling of any desired quantity of the culture medium in admixture with the nutritive substance powder or for combination therewith upon mixture with water.

Because the powder is synthetized, its physical-chemical characteristics are easily controlled, monitored and standardized and thus it is possible to produce culture mediums under standard conditions and with standard effects and properties.

In the dry state, the powder absorbs nutritive substances of the culture medium on its surfaces, a fact which is promoted by the use of the powder in the form of small flakes. This permits packaging of the gel-forming powder together with the culture medium in a package, either in the form of granules into which the flakes can be compressed or agglomerated or in the form of mixtures of the powders, granules and components in a package with or without the pulverulent nutritive components.

The microbiologists can store the powder at ambient temperature and for comparatively long periods (greater than a year) and can also maintain in storage a large variety of dry culture medium packages of any powder which can be prepared in gel form in a matter of minutes without loss of properties.

We claim:

1. A gel-forming compound consisting essentially of unbranched interlaced polygalactan chains of alternating unbranched D and L galactose forms, said chains having a molecular weight between 6000 and 15,000 Daltons, bonded to grains of metallic oxides in the form of a complex as distinguished from a simple mixture, wherein said metal oxides are selected from the group consisting of aluminum oxide, silicon dioxide, and titanium oxide.

2. The gel-forming compound defined in claim 1 wherein the proportion of metal oxide in said compound is between 10 and 80% by weight and varies in inverse proportion to the length of said chains.

3. The gel-forming compound defined in claim 2 in the form of compacts formed by compression of particles of the compound.

4. The gel-forming compound defined in claim 2 in the form of granules consisting of agglomerates of particles of the compound in powder form.

5. The gel-forming compound defined in claim 2 in the form of dry flakes having a film thickness of at most one hundredth of a millimeter.

6. The gel-forming compound defined in claim 2 which is in solution in water at a temperature of about 80° C.

* * * * *